United States Patent [19]

Shimizu et al.

[11] Patent Number: 4,600,507
[45] Date of Patent: Jul. 15, 1986

[54] FILTER DEVICE FOR LIQUIDS

[75] Inventors: Atsushi Shimizu, Tokyo; Sadami Ohtsubo, Honmachi, both of Japan

[73] Assignee: Terumo Kabushiki Kaisha, Tokyo, Japan

[21] Appl. No.: 627,765

[22] Filed: Jul. 5, 1984

[30] Foreign Application Priority Data

Oct. 6, 1983 [JP] Japan .................................. 58-185867

[51] Int. Cl.[4] .............................................. B01D 33/00
[52] U.S. Cl. .................................. 210/94; 210/433.2; 210/445; 210/500.2; 210/512.1; 210/927; 210/500.26; 210/500.27; 210/500.33; 210/500.34; 210/500.36; 210/500.42; 422/101
[58] Field of Search ...................... 210/782, 94, 321.1, 210/321.2, 500.2, 512.1, 927, DIG. 24, 358, 445, 433.2, 905; 422/99, 101; 494/16, 36; 604/4, 6

[56] References Cited

U.S. PATENT DOCUMENTS

| | | | |
|---|---|---|---|
| 1,749,730 | 3/1930 | Kenney | 210/445 |
| 2,341,414 | 2/1944 | Polivka | 210/445 |
| 3,802,843 | 4/1974 | Kim | 422/101 |
| 4,092,113 | 5/1978 | Hardy | 210/927 |
| 4,131,549 | 12/1978 | Ferrara | 210/927 |
| 4,295,974 | 10/1981 | Cornell | 210/927 |
| 4,426,295 | 1/1984 | Evans et al. | 210/927 |

FOREIGN PATENT DOCUMENTS 2923529 12/1980 Fed. Rep. of Germany .

Primary Examiner—Richard V. Fisher
Assistant Examiner—Wanda L. Millard
Attorney, Agent, or Firm—Frishauf, Holtz, Goodman & Woodward

[57] ABSTRACT

A filter device capable of simultaneously effecting centrifugal separation and filtration comprises a hollow main body closed at one end thereof and adapted for effective use in a centrifuge, at least one filter medium disposed inside the hollow main body substantially along the axis thereof and adapted to partition the interior of the hollow main body into plural compartments, at least one of the compartments being a liquid feeding compartment and another compartment being a filtrate receiving compartment, wherein liquid entering the liquid feeding compartment is centrifuged and simultaneously filtered by the filter medium, and the filtrate flows into the filtrate receiving compartment. This filter device is used, for example, for the removal of proteins from blood.

20 Claims, 8 Drawing Figures

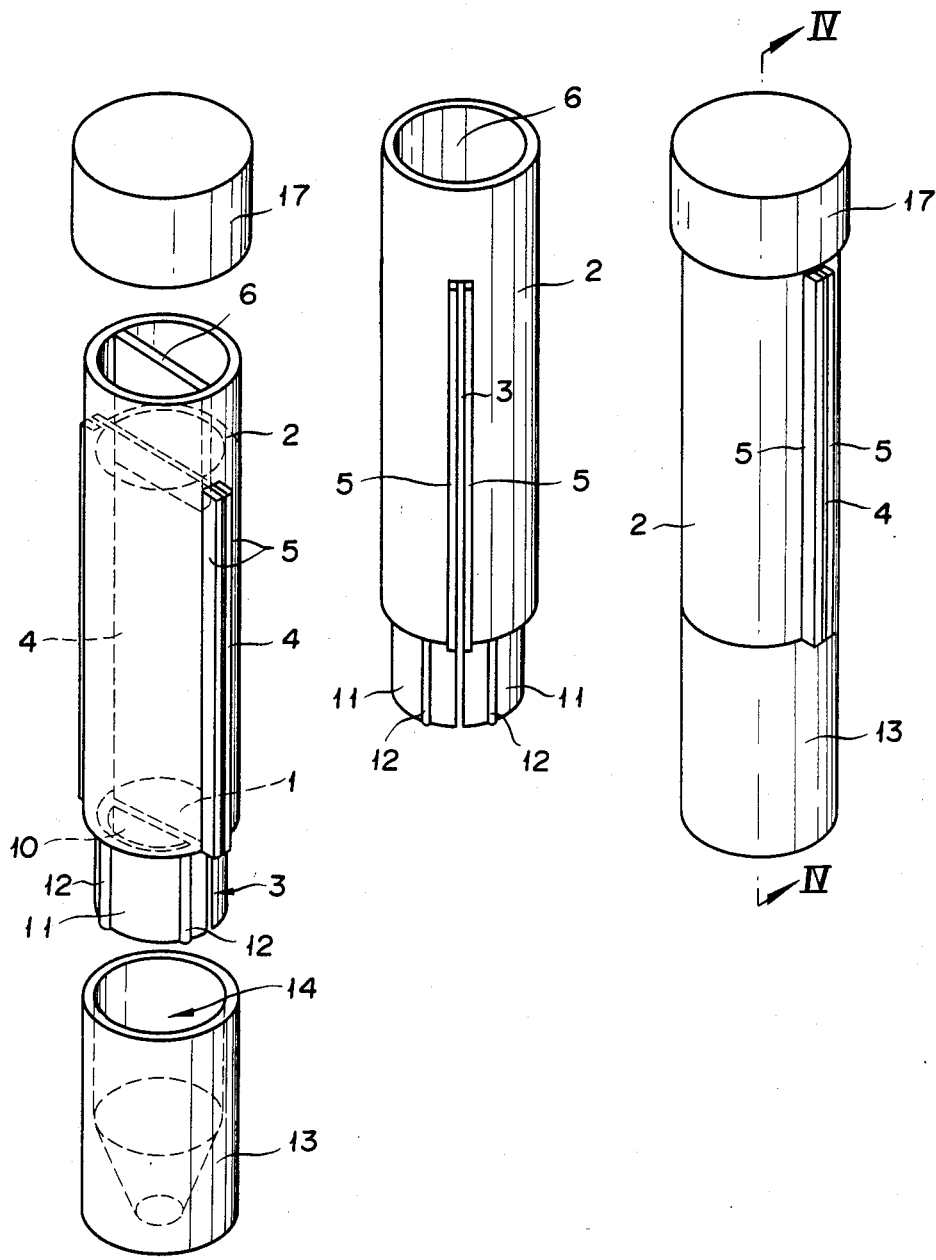

FILTER DEVICE FOR LIQUIDS

BACKGROUND OF THE INVENTION

1. Field of the Invention:

This invention relates to a filter device for liquids. More particularly, this invention relates to a filter device for removing blood cells and proteins from body fluids such as blood and blood plasma particularly by means of centrifugal separation.

2. Description of Prior Art:

In the field of clinical examination, chemical testing on blood is conducted in most cases by a procedure which comprises collecting a blood sample from a subject, allowing the blood sample to stand and coagulate at room temperature for 30 minutes to one hour, centrifuging the coagulated blood for 15 to 20 minutes thereby separating it into blood serum and blood plasma, adding to the blood serum such a protein coagulant as trichloroacetic acid or tungstic acid thereby coagulating proteins contained therein, and subjecting the blood serum to centrifugation thereby obtaining blood serum free from proteins, or further removing proteins the blood plasma. When the chemical test is conducted on other body fluids such as urine or spinal fluid, there are many test items which necessitate removal of proteins.

Generally when coagulated whole blood or coagulationproofed blood is separated by centrifugation into blood serum or blood plasma and the blood serum or blood plasma is further treated for removal of proteins, the practice of adding to the blood an acid solution and subsequently centrifuging the blood to isolate supernatant is followed. This practice is applied similarly to other body fluids such as urine and spinal fluid. This method is such that (a) the operation is troublesome and (b) during the separation of the blood serum, the operation must be conducted with meticulous care lest blood cells or settled proteins should mingle into the blood serum being removed. A blood collection tube containing gel has been suggested as a device enabling the operations of (a) and (b) to be performed with ease. This device has a disadvantage that blood cells remaining after the separation of blood serum is unfit for any further use. Further in the test of blood for detection of a chemical substance (d), the practice of separating chemical substances bound to proteins and free low molecular chemical substances and determining their respective concentrations independently has been gaining in popularity. In this case, again, the removal of proteins constitutes an indispensable step. As a device for centrifugally separating such proteins by means of a filter, there has been suggested a filter device which comprises a cylindrical container and a filter disposed within the container perpendicularly to the axis of the container. In the case of this device, when it is used particularly in a mobile balancing type centrifugal separator, its efficiency of filtration is extremely low because proteins are deposited on the entire surface of the filter. When this device is used for isolation of blood cells from whole blood, it provides practically no filtration because blood cells clog the fine pores of the filter. Even when the device is used in an angle-type centrifugal separator, it fails to provide desired filtration with added efficiency.

An object of this invention, therefore, is to provide a novel filter device for liquids.

Another object of this invention is to provide a filter device for the removal of blood cells and proteins from body bluids such as blood, blood plasma, urine and spinal fluid by means of centrifugation.

SUMMARY OF THE INVENTION

The objects described above are accomplished by a filter device for liquids, which comprises a hollow main body closed at one end thereof and adapted for effective use in a centrifuge, at least one filter medium filtering said liquids disposed inside the hollow main body substantially along the axis thereof and adapted to partition the interior of the cylindrical main body to plural compartments, at least one of said compartments acting as a liquid feeding compartment and another compartment acting as a filtrate receiving compartment, wherein liquids entering the liquid feeding compartment is centrifuged and simultaneously filtered by said filter medium, and the filtrate is flowed into said filtrate receiving compartment.

This invention also embraces a filter device which has a filter medium inserted into and water-tightly nipped by a slit formed substantially along the axis of a hollow main body thereof. This invention further embraces a filter device for liquids, which has a filter medium inserted inside a hollow main body thereof substantially along the axis of the hollow main body. Further, this invention embraces a filter device for liquids, which has a hollow main body formed of at least two component members divided substantially along the axis thereof and has a filter medium water-tightly nipped between the component members of the hollow main body. This invention also embraces a filter device for liquids, which has at least two component members of the hollow main body thereof provided on the periphery thereof with split flanges and has a filter medium nipped along the peripheral edge thereof between the split flanges and fused in situ water-tightly to the split flanges. This invention further embraces a filter medium for liquids, which has a hollow main body and a filtrate receptacle both made of transparent synthetic resin.

This invention further embraces a filter device for liquids further comprising an opening part formed on the closed end side of the filtrate receiving compartment partitioned by said filter medium and a filtrate receptacle fitted in said opening part. This invention further embraces a filter device for liquids further comprising a lid member at an opening part of the liquid feeding compartment. This invention further embraces a filter device for liquids, wherein the lid member is made of a resilient material capable of being punctured by a hollow needle. This invention further embraces a filter device for liquids, wherein a bottom of the liquid feeding compartment is higher than a bottom of the liquid receiving compartment.

BRIEF DESCRIPTION OF THE DRAWINGS

FIG. 1 is a perspective view illustrating the component members of a filter device of this invention for the removal of proteins, FIG. 2 is perspective view illustrating a hollow main body before attachment of a filter medium thereto, FIG. 3 is a perspective view illustrating the filter device in a state prepared for use.

PREFERRED EMBODIMENT OF THE INVENTION

Figures 4, 5, 6, 7:
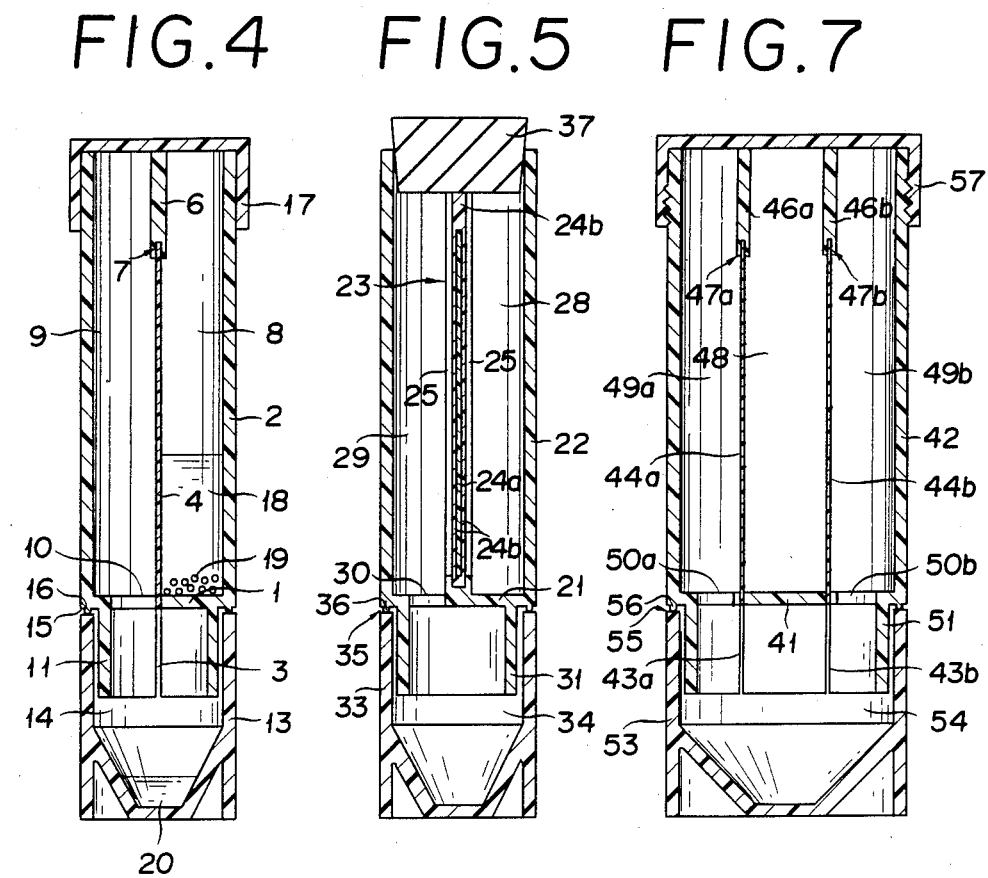
FIG. 4 is a cross sectional view taken along the line VI—VI of the diagram of FIG. 3.
FIG. 5 is a cross sectional view illustrating another embodiment of this invention.
FIG. 6 is a perspective view of a filter medium to be used in the filter device illustrated in FIG. 5.
FIG. 7 is a cross sectional view illustrating yet another embodiment of this invention.

Now, this invention will be described in detail below with reference to the accompanying drawings. As illustrated in FIGS. 1-4, diametrically opposed slits 3 are cut in the wall of a hollow main body 2 such as cylindrical main body having a closed end 1 on the lower side thereof and a filter medium 4 such as, for example, filter paper, filter cloth or filter membrane of synthetic resin which is not permeable to proteins of molecular weights exceeding a fixed level is inserted through the slits 3, nipped between projected strips 5 formed on the edges of the slits, and fastened to the projected strips 5 as by ultrasonic fusion, thermal fusion or adhesion, with the upper end of the filter medium 4 inserted and sealed fast in a slender groove 7 formed in the lower edge of a partition 6 formed either integrally with or separately of the aforementioned hollow main body in the proximity of the open end of the hollow main body 2. In this case, the upper end of the filter medium is not always required to be inserted into the slender groove 7 and may be instead fastened to the lower edge as by ultrasonic fusion, thermal fusion or adhesion. Optionally, the aforementioned partition wall 6 may be omitted. The main body 2 of the filter device is not exclusively required to be in a cylindrical shape. It may be formed in the shape of an angular column or 8 letter shape in cross section.

The interior of the hollow main body 2, therefore, is partitioned by the filter medium 4 into two compartments (a liquid feeding compartment 8 and a filtrate receiving compartment 9). One of the compartments (the filtrate receiving compartment 9) has an opening part 10 formed on the closed end side thereof. A hollow connecting part 11 formed in the proximity of the opening part 10 optionally has ribs 12 formed on the outer wall thereof. A filtrate receptacle 13 is fitted around the hollow connecting part 11 substantially in intimate contact with the outer wall of the hollow connecting part 11 or with the apexes of the ribs 12. The interior 14 of the filtrate receptacle 13 communicates with the filtrate receiving receiving compartment 9 via the aforementioned opening 10. The interior of the filtrate receptacle 13 has its bottom part formed in the shape of a funnel. In this case, a protuberance 16 may be formed on the part 15 of the hollow main body 2 destined to collide against the upper part of the filtrate receptacle 13 or a protuberance (not shown) may be formed on the upper part of the filtrate receptacle 13. The protuberance will facilitate flow of the air when the filtrate flows in and displaces the air remaining inside during the course of centrifugal filtration as described afterward. When the aforementioned opening 10 has an ample area, however, no special gap is required for escape of the air being displaced. On the contrary, this opening may be sealed as with a packing or an O-ring. A lid 17 is fitted around the opening end of the cylindrical main body 2. When the partition wall 6 is absent from the hollow main body 2 or when it is formed recessed inside of the upper edge surface of the main body 2, 6, a rubber stopper 37 may be inserted in the opening.

FIG. 5 represents another embodiment of this invention. Two pairs of parallel projected strips 25 are formed as diametrically opposed to each other on the inner wall of a hollow main body 22 having a closed end 21 on the lower side thereof and a filter member having a filter medium 24a held fast in place with a surrounding frame 24b is inserted in grooves defined by the paired projected strips 25. The filter member, when required, may be fastened to the projected strips as by ultrasonic fusion, thermal fusion or adhesion. In this manner, the interior of the hollow main body 22 is partitioned by the filter medium 24a into two compartments (a liquid feeding compartment 28 and a filtrate receiving compartment 29). One of the compartments (the filtrate receiving compartment 29) has an opening part 30 formed on the closed end side thereof. A hollow connecting part 31 which is formed in the proximity of the opening 30 has ribs formed, when required, thereon in much the same way as in the embodiment of FIG. 1. A filter receptacle 33 is fitted around the hollow connecting part 31 in contact with the outer wall of the hollow main body 3 or with the apexes of the ribs. The interior 34 of the filtrate receptacle 33 communicates with the filtrate receiving compartment 29 through the aforementioned opening 30. In this case, a protuberance 36 may be formed on the part 35 of the hollow main body 22 destined to collide against the upper part of the filtrate receptacle 33 or a protuberance (not shown) may be formed on the filtrate receptacle 33. The protuberance will facilitate flow of the air when the filtrate flows in and displaces the air remaining inside during the course of the centrifugal filtration as described afterward. A lid 37 such as, for example, a rubber stopper is inserted in the opening end of the hollow main body 22. In this case, the lid 37 may be in the form of a cap adapted to be fitted around the opening end.

FIG. 7 represents yet another embodiment of this invention. This filter device is similar in construction to the filter device of FIGS. 1-4 and has a relatively large inner volume. In this case, two pairs of slits 43a, 43b are cut in the wall of a hollow main body 42 along the axis of the hollow main body and filter mediums 44a, 44b are inserted through the slits 43a, 43b an nipped between the projected strips (not shown) formed on the edges of the slits 43a, 43b and fastened to the projected strips as by ultrasonic fusion, thermal fusion or adhesion, with the upper ends of the filtrate mediums inserted and retained fast in grooves 47a, 47b formed in the lower edges of partition walls 46a, 46b formed integrally with or independently of the aforementioned hollow main body 42 in the proximity of the aforementioned opening end. In this case, the upper ends of the filter mediums are not always required to be inserted into the groves 47a, 47b and may be instead fastened to the lower edges of the aforementioned partition walls 46a, 46b as by ultrasonic fusion, thermal fusion or adhesion. The aforementioned partition walls 46a, 46b may be omitted as occasion demands.

The interior of the hollow main body 24, accordingly, is partitioned into three compartments (a liquid feeding compartment 48 and filtrate receiving compartments 49a, 49b) by the filter mediums 44a, 44b. The outer compartments (filtrate receiving compartments 49a, 49b) have opening parts 50a, 50b formed respectively on the closed end side thereof. The other component members of the filter device are identical with those used in the filter device of FIGS. 1–4. The numerals used in FIGS. 1–4 plus 40 denote like component parts in FIG. 7. This invention embraces a modified embodiment having a similar constitution except that the liquid feeding compartment and the liquid receiving compartment were exchanged each other in FIG. 2.

Optionally, the embodiments so far may be modified by having the respecively partitioned compartments (filtrate receiving compartments 9, 29, 49a and 49b) substituted by removable containers which are similar to the compartments except that the opening parts 10, 30, 50a and 50b are closed and which are adapted to be disposed in the same positions as the compartments 9, 29, 49a and 49b or in the positions below the bottoms of the compartments 9, 29, 49a and 49b.

Figure 8:
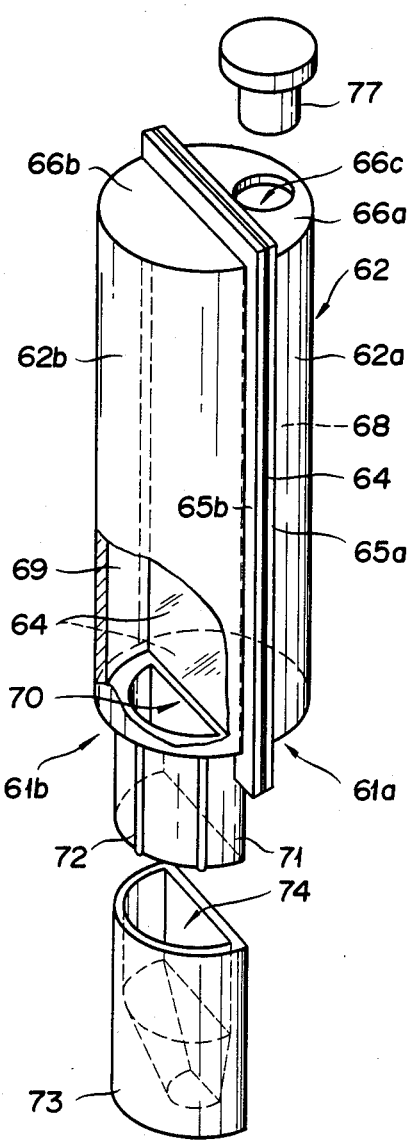
FIG. 8, is a perspective view illustrating a further embodiment of this invention.

FIG. 8 represents still another embodiment of this invention. In this filter device, first and second component members 62a, 62b form a hollow main body having closed ends 61a, 61b respectively on one side thereof and having flanges 65a, 65b formed on the rectangular edges thereof along the axis of the hollow main body which are joined to each other, with the flanges 65a, 65b having a filter medium 64 and watertightly sealed thereto in situ as by high-frequency, thermal or ultrasonic fusion, or by adhesion with an adhesive, to complete the hollow main body 62. The first component members 62a has an inlet 66c perforated in the other end 66a thereof and adapted to be stoppered with a cap 77. The first component member 62a and the filter medium 64 enclose therewith a liquid feeding compartment 68. The second component member 62b has the closed end formed on the other end 66b. The closed end 61b on the opposite end has an opening part 70 formed therein. The second component member 62b and the filter medium 64 enclose therewith a filtrate receiving compartment 69. Further, on the opening part 70 of the second component member, there is formed a hollow connecting part 71. Optionally, this hollow connecting part 71 has ribs formed on the outer wall surface thereof. A filtrate receptacle 73 is fitted around the hollow connecting part 71 substantially in contact with the outer wall surface of the hollow connecting part 71 or with the apexes of the ribs 72. The interior 74 of the filtrate receptacle 73 communicates with the filtrate receiving compartment 69 via the aforementioned opening part 70. Further, the interior 74 of the filtrate receptacle 73 may have the bottom part thereof formed in the shape of a funnel. The present invention requires that the filter medium be fixed in the hollow main body thereof substantially along the axis of the hollow main body. If the filter medium is disposed in the filter device in such a position that the plane containing the filter medium falls substantially perpendicularly to the direction of centrifugation during the centrifugal separation, then the solid particulate substance (the component not passed by the filter) clogs the pores of the filter medium. For the prevention of this trouble, therefore, it suffices to have the filter medium disposed so that the aforementioned plane will fall substantially in the direction of centrifugation.

In the filter device in accordance with the present invention, it is preferable to provide a lid member at the opening part of the liquid feeding compartment.

In another embodiment, the hollow main body may be prepared as an air-tight body providing a lid member of a resilient material capable of being punctured by a hollow needle such as a syringe, or cannula and the interior of the hollow main body may be maintained at a reduced pressure. In such case, the body liquid can be collected and separated by reducing the pressure therein under a complete closed system. Thus contamination of the body liquid can be avoided. Further, the bottom of the liquid receiving compartment may be made of the reslient material. In such case, sampling of the filtrate is possible by puncturing the hollow needle to the resilient bottom. In such case, it is preferable that the bottom of the liquid feeding compartment is higher than the bottom of the liquid receiving compartment.

The material selected for the aforementioned hollow main body is not critical. Since the filter device of this invention is subjected to the action of centrifugal separation as described afterward, the hollow main body, the lid, the filtrate receptacle, etc. mentioned above are desired to be made of a material capable of enduring a centrifugal force of the order of 1200 G. Examples of a material of such durability include glass, polypropylene, rigid vinyl chloride resin, polyethylene terephthalate, ABS resin, polymethacrylate and polystyrene. Synthetic resin of high transparency is an ideal choice. The rubber stopper may be made of natural rubber or synthetic rubber such as styrene-butadiene rubber, choroprene rubber, nitrile rubber, butyl rubber or urethane rubber.

As the material for the fillter medium, membrane, filter paper or filter cloth having ample strength and containing uniform pores capable of passing low molecular substances and incapable of passing proteins of molecular weights exceeding a fixed level (such as, for example, 20,000 to 50,000). Example of the material fulfilling the requirement include polyamide, polyethylene terephthalate, polysulfones, cellulose such as cellulose acetate, cellulose nitrate and regenerated cellulose, acrylic resins such as polyacrylonitrile, polypropylene, polyvinyl alcohol, vinyl chloride resin, etc. When the filter device uses a membrane containing pores 1 to several microns in diameter, it provides easy separation of blood plasma and blood cells from whole coagulationproofed blood. Alternatively as the filter medium, a membrane for ultrafiltration in which no micropores are intentionally formed may be adopted.

The filter medium may be provided under curving projected to the liquid receiving compartment side, for example, along with the wall of the liquid receiving compartment, thereby the liquid feeding compartment can be enlarged.

The filter device of this invention is put to use as described below. In case the filter device of construction of FIGS. 1–4 is used for the filtration of body fluid, for example, a sample blood (coagulationproofed whole blood or whole blood not proofed against coagulation) 18 is injected through the opening part of the hollow main body 2 into the liquid feeding compartment 8. Then, the lid 17 is fastened to the opening part of the hollow main body 2. Now, the filter device is set in place in a centrifugal separator (not shown) in such a manner that the filtrate receptacle 13 will fall on the outer side in the direction of centrifugation. The centrifugal separator is then operated for 10 to 15 minutes, with the centrifugal force fixed in the neighborhood of 1200 G. Under the influence of the centrifugal force, blood cells 19 first settle to the bottom of the liquid feeding compartment. Of the high molecular proteins, those which have coagulated settle to the bottom and those which have not yet coagulated gradually move downwardly from the bottom inwardly, the high molecular proteins and distributed in the pattern of density gradient. In the sample under treatment, the centrifugal force is exerted downwardly and the repulsive force in all the other directions. Consequently, water, low molecular components and blood plasma are passed through the lower part of the filter medium 4 in which the repulsive force to the centrifugal force is greatest and the resisting force is minimal. This region of filtration shifts upwardly as particulate components such as proteins clog the pores of the filter medium. The filtrte 20 which has passed the filter medium 4 moves into the filtrate receiving compartment 9 and immediately flows into the interior 14 of the filtrate receptacle 13 via the opening part 10. At this time, the air inside the filtrate receptacle 13 is discharged through the gap to be formed between the outer surface of the hollow connecting part 11 and the inner surface of the filtrate receptacle 13 by virtue of the ribs 12. By this procedure, all the components of the blood under treatment to be filtered are passed through the filter medium without entailing the phenomenon of clogging.

The operation of the filter device has been described as applied to the filtration of blood (whole blood). It similarly applies to other kinds of body fluid such as blood plasma, blood serum, urine and spinal fluid.

The filter devices constructed as shown in FIGS. 5-8 are operated by the same procedure.

Now, the effect of the present invention will be described below with reference to working examples.

EXAMPLE 1

Filter devices for liquids were made of polypropylene in a construction as shown in FIGS. 1-4 and polyamide-type filter membranes (differential molecular weight 20,000) (surface area 0.9 cm$^2$) were fixed in place therein by thermal fusion. The filter devices, with 1 ml of coagulationproofed blood (whole blood) placed each in the liquid feeding compartments 8 thereof, were set one each in a balance type (Model CPN-005, made by Shimadzu Corporation) and an angle type (Model K-8, table-top type, made by Kubota Ltd.) centrifugal separators and were subjected to centrifugal separation with centrifugal force of about 1200 G (3000 rpm) for 10 minutes. The results were as shown in Table 1.

EXAMPLE 2

The procedure of Example 1 was repeated, except that blood serum was used in the place of whole blood. The results were as shown in Table 2.

CONTROL 1

The procedure of Example 1 was repeated, except that conventional filter devices (with the same filter mediums as those of Example 1 fixed in place in planes perpendicular to the direction of centrifugation) for removal of proteins were used in the place of filter devices of the construction of FIGS. 1-4. The results were as shown in Table 1.

CONTROL 2

The procedure of Control 1 was repeated, except that blood serum was used in the place of whole blood. The results were as shown in Table 2.

TABLE 1

| Run No. | Balance type | | Angle type | |
| --- | --- | --- | --- | --- |
| | Example 1 | Control 1 | Example 1 | Control 1 |
| 1 | 0.33 | 0 | 0.30 | 0.1 |
| 2 | 0.35 | 0.01 | 0.35 | 0.3 |

TABLE 1-continued

| Run No. | Balance type | | Angle type | |
| --- | --- | --- | --- | --- |
| | Example 1 | Control 1 | Example 1 | Control 1 |
| 3 | 0.32 | 0.005 | 0.20 | 0.3 |
| Average | 0.33 | 0.005 | 0.28 | 0.3 |

*Unit: ml

TABLE 2

| Run No. | Balance type | | Angle type | |
| --- | --- | --- | --- | --- |
| | Example 1 | Control 1 | Example 1 | Control 1 |
| 1 | 0.35 | 0.05 | 0.35 | 0.15 |
| 2 | 0.40 | 0.06 | 0.23 | 0.20 |
| 3 | 0.37 | 0.05 | 0.33 | 0.17 |
| Average | 0.37 | 0.05 | 0.30 | 0.17 |

*Unit: ml
**The protein concentrations after filtration were invariably below 60 µg/ml.

As described above, the filter device for liquids according to this invention comprises a hollow main body closed at one end thereof and adapted for effective use in a centrifugal separator, at least one filter medium disposed inside the cylindrical main body substantially along the axis thereof and adapted to partition the interior of the cylindrical main body, an opening part formed on the closed end side of one of the compartments partitioned by the filter medium, a filtrate receptacle fitted in the opening part, and a lid attached to the open end of the cylindrical main body. When a body fluid is centrifuged by the use of this filter device, therefore, such solid particulate components as proteins and blood cells are caused by the centrifugal force to settle in the bottom of the cylindrical main body and such filtering components as blood plasma and blood serum are caused by the repulsive force against the centrifugal force to pass through the filter medium disposed substantially parallelly to the direction of the centrifugal force without inducing settlement of solid particular components and enter the other compartment and, at the same time, flow into the filtrate receptacle via the opening part formed at the bottom of the compartment. Thus, the filtration can be effected perfectly without clogging the filter medium at all. Even proteins of relatively small molecular weights are not caused by the centrifugal force to move in the direction of the filter medium but allowed to move to the bottom lying in the direction of the centrifugal force. They coagulate in the bottom and are not allowed to pass through the filter medium. They are separated from the filtrate. Since the filter medium does not experience the phenomenon of clogging, it can treat a large volume of liquid for its small surface area. In the collection of blood serum freed from proteins, the conventional filter device necessitates a procedure which comprises allowing a given sample of whole blood to stand and coagulate for 30 to 60 minutes, then centrifuging the coagulated whole blood for 15 to 20 minutes, causing the separated supernatant (blood serum) and trichloroacetic acid or tungstic acid added thereto to stand for 10 to 15 minutes thereby inducing precipitation, and further centrifuging the resultant mixture for about 10 minutes. As compared with the conventional filter device which requires the operation of the centrifugal separator twice, the filter device of this invention is advantageous in respect that just one centrifugal separation suffices. Further, since the solid particulate components separated by the filter device of this invention are coagulated during the course of centrifugal separation, the time heretofore required for their standing is no longer necessary. The meticulous care heretofore required in preventing blood serum from rising and mingling into the separated supernatant is not required by the filter device of this invention.

What is claimed is:

1. A filter device for use in centrifuging liquids containing at least one solid component therein, the filter device comprising:
    a hollow main body having a longitudinal axis and being closed at one end thereof, and for receiving liquids therein;
    at least one filter medium mounted inside said hollow main body for filtering a liquid in said hollow main body, said at least one filter medium being disposed substantially along the axis of said hollow main body and partitioning the interior of said hollow main body into at least a liquid feeding compartment and a filtrate receiving compartment;
    said hollow main body including a filtrate receptacle at the bottom thereof, said filtrate receptacle being in communication with said filtrate receiving compartment;
    said hollow main body having feeding means coupled to said liquid feeding compartment for feeding said liquid containing at least one solid component into said liquid feeding compartment; and
    said at least one filter medium having a longitudinal length in the direction of said axis of said main body which is greater than the depth of liquid in said liquid feeding compartment, whereby during centrifuging, said liquid in said liquid feeding compartment is centrifuged and simultaneously filtered by said at least one filter medium, and a filtrate flows through said at least one filter medium and into said filtrate receiving compartment.

2. The filter device of claim 1, wherein said hollow main body comprises at the lower portion thereof a hollow connecting part, said filtrate receptacle being coupled around said hollow connecting part.

3. The filter device of claim 2, wherein at least one of said hollow connecting part and said filtrate receptacle comprise ribs on a surface thereof, the other of said hollow connecting part and filtrate receptacle being fitted around and in contact with apexes of said ribs.

4. The filter device of claim 3, wherein said ribs are provided on the outer wall surface of said hollow connecting part, and said filtrate receptacle comprises an inner wall surface fitted around said hollow connecting part in contact with the apexes of said ribs.

5. The filter device of claim 1, wherein said hollow main body and said filtrate receptacle are made of a transparent synthetic resin material.

6. A filter device for use in centrifuging liquids containing at least one solid component therein, the filter device comprising:
    a hollow main body having a longitudinal axis and being closed at one end thereof, and for receiving liquids therein;
    at least one filter medium mounted inside said hollow main body for filtering a liquid in said hollow main body, said at least one filter medium being disposed substantially along the axis of said hollow main body and partitioning the interior of said hollow main body into at least a liquid feeding compartment and a filtrate receiving compartment;
    said at least one filter medium being water-tightly connected to said hollow main body inside of said hollow main body substantially along said axis of said hollow main body;
    said hollow main body having feeding means coupled to said liquid feeding compartment for feeding said liquid containing at least one solid component into said liquid feeding compartment; and
    said at least one filter medium having a longitudinal length in the direction of said axis of said main body which is greater than the depth of liquid in said liquid feeding compartment, whereby during centrifuging, said liquid in said liquid feeding compartment is centrifuged and simultaneously filtered by said at least one filter medium, and a filtrate flows through said at least one filter medium and into said filtrate receiving compartment.

7. The filter device of claim 6, further comprising means defining an opening at the closed end side of said filtrate receiving compartment, and a filtrate receptacle coupled to said opening defining means.

8. The filter device of claim 7, wherein said liquid feeding compartment has means defining an open end as the end thereof opposite said closed end of said hollow main body, and further comprising a lid member selectively closing said open end defining means of said liquid feeding compartment.

9. The filter device of claim 6, wherein said liquid feeding compartment has means defining an open end at the end thereof opposite said closed end of said hollow main body, and further comprising a lid member selectively closing said open end defining means of said liquid feeding compartment.

10. The filter device of claim 9, wherein said lid member is made of a resilient material which is puncturable by a hollow needle.

11. The filter device of claim 6, wherein the liquid feeding compartment has a bottom which is higher than a bottom of said filtrate receiving compartment.

12. The filter device of claim 6, wherein said at least one filter medium is a substantially flat member having elongated side edges, said elongated side edges being watertightly connected inside said hollow main body substantially along said axis of said hollow main body.

13. A filter device for use in centrifuging liquids containing at least one solid component therein, the filter device comprising:
    a hollow main body having a longitudinal axis and being closed at one end thereof, and for receiving liquids therein;
    at least one filter medium mounted inside said hollow main body for filtering a liquid in said hollow main body, said at least one filter medium being disposed substantially along the axis of said hollow main body and partitioning the interior of said hollow main body into at least a liquid feeding compartment and a filtrate receiving compartment;
    said hollow main body comprising at least two component members divided substantially along said axis of said hollow main body, said at least two component members being connected together with said at least one filter medium water-tightly connected between said interconnected component members;
    said hollow main body having feeding means coupled to said liquid feeding compartment for feeding said liquid containing at least one solid component into said liquid feeding compartment; and
    said at least one filter medium having a longitudinal length in the direction of said axis of said main body which is greater than the depth of liquid in said liquid feeding compartment, whereby during centrifuging, said liquid in said liquid feeding compartment is centrifuged and simultaneously filtered by said at least one filter medium, and a filtrate flows through said at least one filter medium and into said filtrate receiving compartment.

14. The filter device of claim 13, wherein said at least two component members have flanges formed on edges thereof, and said at least one filter medium is water-tightly sealed between said flanges of said component members, peripheral portions of said at least one filter medium being interconnected between said flanges.

15. The filter device of claim 14, wherein said peripheral portions of said at least one filter medium are fused to said flanges.

16. A filter device for use in centrifuging liquids containing at least one solid component therein, the filter device comprising:
a hollow main body having a longitudinal axis and being closed at one end thereof, and for receiving liquids therein;
at least two filter mediums mounted inside said hollow main body for filtering a liquid in said hollow main body, said at least two filter mediums being spaced apart from each other in the radial direction of said hollow body and being disposed substantially along the axis of said hollow main body, said at least two filter mediums partitioning the interior of said hollow main body so as to define a liquid feeding compartment between two of said at least two filter mediums and two filtrate receiving compartments between the respective filter mediums and interior walls of said hollow main body;
said hollow main body having feeding means coupled to said liquid feeding compartment for feeding said liquid containing at least one solid component into said liquid feeding compartment; and
said at least two filter mediums having a longitudinal length in the direction of said axis of said main body which is greater than the depth of liquid in said liquid feeding compartment, whereby during centrifuging, said liquid in said liquid feeding compartment is centrifuged and simultaneously filtered by said at least two filter mediums, and a filtrate flows through said at least two filter mediums and into said filtrate receiving compartments.

17. The filter device of claim 16, further comprising means defining respective openings at the closed end sides of said filtrate receiving compartments, and a filtrate receptacle coupled to said closed end side of said hollow main body and in communication with said means defining said openings.

18. A filter device for use in centrifuging liquids containing at least one solid component therein, the filter device comprising:
a hollow main body having a longitudinal axis and being closed at one end thereof, and for receiving liquids therein;
said hollow main body having a wall having slits therein, said slits extending substantially along said axis of said hollow body;
at least one filter medium mounted inside said hollow main body for filtering a liquid in said hollow main body, said at least one filter medium being received in said slits and being disposed substantially along said axis of said hollow main body and partitioning the interior of said hollow main body into at least a liquid feeding compartment and a filtrate receiving compartment;
said hollow main body having feeding means coupled to said liquid feeding compartment for feeding said liquid containing at least one solid component into said liquid feeding compartment; and
said at least one filter medium having a longitudinal length in the direction of said axis of said main body which is greater than the depth of liquid in said liquid feeding compartment, whereby during centrifuging, said liquid in said liquid feeding compartment is centrifuged and simultaneously filtered by said at least one filter medium, and a filtrate flows through said at least one filter medium and into said filtrate receiving compartment.

19. The filter device of claim 18, wherein said respective slits have opposing edges, said filter medium being water-tightly nipped between said edges of said slits.

20. A filter device for use in centrifuging liquids containing at least one solid component therein, the filter device comprising:
a hollow main body having a longitudinal axis and being closed at one end thereof, and for receiving liquids therein, said hollow main body including a wall having slits therein, said slits extending substantially along said axis of said hollow body;
at least one filter medium mounted inside said hollow main body for filtering a liquid in said hollow main body, said at least one filter medium being disposed substantially along the axis of said hollow main body and partitioning the interior of said hollow main body into at least a liquid feeding compartment and a filtrate receiving compartment;
said hollow main body having feeding means coupled to said liquid feeding compartment for feeding said liquid containing at least one solid compartment into said liquid feeding compartment;
said at least one filter medium having a longitudinal length in the direction of said axis of said main body which is greater than the depth of liquid in said liquid feeding compartment;
means defining an opening in said filtrate receiving compartment at the closed end side of said hollow main body; and
a filtrate receptacle coupled to said hollow main body at the closed end side thereof via said opening defining means and in communication with said filtrate receiving compartment for receiving a filtrate from said filtrate receiving compartment, whereby during centrifuging, said liquid in said liquid feeding compartment is centrifuged and simultaneously filtered by said at least one filter medium, and the filtrate flows through said at least one filter medium into said filtrate receiving compartment and then into said filtrate receptacle.

* * * * *

UNITED STATES PATENT AND TRADEMARK OFFICE
CERTIFICATE OF CORRECTION

PATENT NO. : 4,600,507

DATED : July 15, 1986

INVENTOR(S) : Atsushi SHIMIZU et al.

It is certified that error appears in the above-identified patent and that said Letters Patent is hereby corrected as shown below:

COLUMN 4, line 1, after "2," delete "6,".

COLUMN 5, line 23, after "medium 64" delete "and".

COLUMN 6, last line, change "and" to --are--.

COLUMN 7, line 9, change "filtrte" to --filtrate--.

Signed and Sealed this

Thirteenth Day of January, 1987

Attest:

DONALD J. QUIGG

Attesting Officer

Commissioner of Patents and Trademarks